United States Patent
Ito et al.

(10) Patent No.: US 9,308,229 B2
(45) Date of Patent: Apr. 12, 2016

(54) METHOD OF INHIBITING ANGIOGENESIS

(71) Applicants: Hiroko Itoh, Mie (JP); Powerful Healthy Food Corporation, Nagano (JP); SUN CHLORELLA CORP., Kyoto (JP)

(72) Inventors: Hitoshi Ito, Mie (JP); Hiroko Itoh, Mie (JP); Masaki Fujishima, Kyoto (JP); Yukari Arakawa, Kyoto (JP); Fukuyoshi Nakada, Nagano (JP)

(73) Assignees: Hiroko Itoh, Mie (JP); Powerful Healthy Food Corporation, Nagano (JP); Sun Chlorella Corp., Kyoto (JP)

( * ) Notice: Subject to any disclaimer, the term of this patent is extended or adjusted under 35 U.S.C. 154(b) by 0 days.

(21) Appl. No.: 14/833,825

(22) Filed: Aug. 24, 2015

(65) Prior Publication Data

US 2015/0359829 A1    Dec. 17, 2015

Related U.S. Application Data

(63) Continuation-in-part of application No. 13/760,616, filed on Feb. 6, 2013.

(30) Foreign Application Priority Data

Jun. 20, 2012 (JP) .................. 2012-139227

(51) Int. Cl.
*A61K 38/16* (2006.01)
*A23L 1/28* (2006.01)
*A61K 36/07* (2006.01)

(52) U.S. Cl.
CPC . *A61K 36/07* (2013.01); *A23L 1/28* (2013.01); *A61K 38/16* (2013.01); *A23V 2002/00* (2013.01)

(58) Field of Classification Search
None
See application file for complete search history.

(56) References Cited

PUBLICATIONS

Mizuno et al., Antitumor Activity and Some Properties of Water-Insoluble Hetero-glycans from "Himemeatsutake," the Fruiting Body of Agaricus blazei Murill, Agric. Biol. Chem., 54(11), 2897-2905 (1990).*

Kimura et al., Isolation of an anti-angiogenic substance from Agaricus blazei Murill: Its antitumor and antimetastatic actions, Cancer Sci, Sep. 2004, vol. 95, No. 9, pp. 758-764.*

* cited by examiner

*Primary Examiner* — Karlheinz R Showronek
*Assistant Examiner* — Joseph Fischer
(74) *Attorney, Agent, or Firm* — McGlew and Tuttle, P.C.

(57) ABSTRACT

A method of inhibiting angiogenesis by applying a kind of protein polysaccharide of a (1→6)-β-D-glucan obtained from a residue of extraction of crushed dried fruiting body of *Agaricus blazei* Murill (himematsutake) with 80% ethanol aqueous solution and hot water at 100 degrees C.

8 Claims, 3 Drawing Sheets

METHOD OF INHIBITING ANGIOGENESIS

CROSS REFERENCE TO RELATED APPLICATIONS

This application is a Continuation in Part of, and claims the benefit of priority under 35 U.S.C. §120 of, application Ser. No. 13/760,616 filed Feb. 6, 2013, which claims the benefit of priority under 35 U.S.C. §119 of foreign application JP 2012-139227 filed on Jun. 20, 2012, the entire contents of which are incorporated herein by reference.

BACKGROUND OF THE INVENTION

1. Field of the Invention

The present invention relates to a method of inhibiting angiogenesis.

2. Description of the Prior Art

Suppression of angiogenesis is thought to lead to suppression of tumor or cancer growth or metastasis, chronic inflammation, rheumatoid arthritis, retinopathy, diabetic retinopathy, age-related macular degeneration, and the like.

It has been reported that an anti-angiogenic action is present in food ingredients such as shark gristle, epigallocatechin (EGC) and epigallocatechin gallate (EGCG), which are components of green tea, genistein, which is a kind of soybean isoflavone, *Agaricus blazei*-derived ergosterol, and pyroglutamic acid.

Regarding the anti-angiogenic actions of substances derived from mushrooms, in addition to the aforementioned action of *Agaricus blazei*-derived ergosterol (Isolation of an anti-angiogenic substance from *Agaricus blazei* Murill: Its antitumor and antimetastatic actions; Kimura et al.; Cancer Sci., September 2004, vol. 95, no. 9, 758-764), the actions of *Trametes versicolor*-derived PSK (Inhibitory effect of PSK on angiogenesis.; Wada T, Wakamatsu Y, et al.; Biotherapy 15(3):389-392, 2001) and *Sparassis crispa*-derived β-1,3-D-glucan have been reported (Anti-angiogenic and Anti-metastatic Effects of β-1,3-D-Glucan Purified from Hanabiratake, *Sparassis crispa*; Kyosuke Yamamoto, Takashi Kimura et al.; Biol. Pharm. Bull. 32(2) 259-263, 2009).

PS-K is a glycoprotein containing about 15% of protein, and comprising 19 amino acids such as aspartic acid and glutamic acid, characterized by a putative structure of a main chain of α- or β-1,4 bonds with 1 branch per 5 glucose groups at the 3- or 6-position (Host effects of polysaccharides on cancer-bearing animals, with a focus on the action of glycoprotein PS-K from *Trametes versicolor*; Shigeru Tsukagoshi; Gan To Kagaku Ryoho (Japanese Journal of Cancer and Chemotherapy), vol. 1, no. 2; pp. 251-257, 1974).

Naohito Ohno et al. reported that the antitumor component of *Sparassis crispa* is 1,3-β-glucan (Antitumor 1,3-β-Glucan from Cultured Fruit Body of *Sparassis crispa*; Naohito Ohno et al.; Biol. Pharm. Bull. vol. 23, No. 7, 866-872, 2000). Furthermore, Yamamoto et al. reported that the component had a pulmonary metastasis suppressing effect and anti-angiogenic action (Anti-angiogenic and Anti-metastatic Effects of β-1,3-D-Glucan Purified from Hanabiratake, *Sparassis crispa*; Kyosuke Yamamoto, Takashi Kimura et al.; Biol. Pharm. Bull. 32(2) 259-263, 2009).

The antitumor activity and antitumor immunological action mechanism of a himematsutake-derived (1→6)-β-D-glucan protein complex have already been reported (Inhibitory Action of a (1→6)-β-D-Glucan-Protein Complex (FIII-2-b) Isolated from *Agaricus blazei* Murill ("Himematsutake") on Meth A Fibrosarcoma-Bearing Mice and Its Antitumor Mechanism; Hiroko Itoh et al.; Jpn. J. Pharmacol. 66, 265-271, 1994), and a patent application for an antitumor agent was filed as described in JP-A-HEI-2-78630.

This (1→6)-β-D-glucan protein complex (hereinafter also referred to as "the polysaccharide") is the first substance of its kind obtained from a mushroom, identified as a polysaccharide comprising 50.2% of sugar moiety and 43.3% of protein moiety (Antitumor Activity and Some Properties of Water-insoluble Hetero-glycans from "Himematsutake," the Fruiting Body of *Agaricus blazei* Murill; Takashi Mizuno et al.; Agric. Biol. Chem., 54(11), 2897-2905, 1990).

Known β-(1→6)-glucans include pustulan, which is known to occur in the lichen *Umbilicaria pustulata*; islandic acid (a polysaccharide comprising a main chain of β-(1→6) bond and a few side chains of 1→4 bond), which is obtained from a culture filtrate of *Penicillium islandicum*; commercially available dextrans with various molecular weights [Dextran] (produced by Pharmacia Co., a glucan comprising a main chain of α-(1→6) bond and a few branched structures); and oat lichenin, which is isolated from the seeds of oat; however, none of these substances possesses antitumor activity against mouse sarcoma 180 or anti-angiogenic action (<Proceedings of Basic Cancer Study Group Symposium> "Criticism on the anticancer effects of polysaccharides": Study of antineoplastic polysaccharides in lichen, with special reference to *Gyrophora esculenta* Miyoshi; Yoshihiro Nishikawa; Nippon Rinsho (Japanese Journal of Clinical Medicine), vol. 27, no. 6; pp. 184-188, 1969).

From the above-described findings, it is suggested that the antitumor activities of polysaccharides may be largely influenced by small differences in their molecular structure and stereochemical factors.

While "the polysaccharide" is known to have the properties described above, there has so far been no knowledge that "the polysaccharide" exhibits anti-angiogenic action.

Regarding the safety of himematsutake (the same himematsutake as that from which "the polysaccharide" was isolated [himematsutake having the same gene sequence of the ITS [internal transcribed spacer] of 5.8S rDNA]), himematsutake was verified to be safe in "Safety research with a focus on the mutagenicity of existing natural food additives and the like" (Health Science Special Research Project) by the Head (Makoto Hayashi) of the Division of Genetics and Mutagenesis in the National Institute of Health Sciences et al. Also in a subchronic toxicity study of himematsutake extract in rats, the safety was verified by Yuichi Kuroiwa et al. at the Division of Pathology in the National Institute of Health Sciences (Lack of subchronic toxicity of an aqueous extract of *Agaricus blazei* Murill in F344 rats; Y. Kuroiwa, et al.; Food and Chemical Toxicology 43(2005) 1047-1053).

SUMMARY OF THE INVENTION

The present invention is intended to provide a method of inhibiting angiogenesis that can be used safely and conveniently for a long period.

[1] It has been discovered that angiogenesis can be inhibited by applying a kind of (1→6)-β-D-glucan-containing product.

In one embodiment of the present invention, there is provided a method of inhibiting angiogenesis by applying a substance obtained by the steps of:

extracting a fruiting body of *Agaricus blazei* Murill (himematsutake) with a lower aliphatic alcohol or a lower aliphatic alcohol containing not more than 20% of water to obtain Residue S, extracting Residue S with hot water to obtain Residue I, extracting Residue I with 1% ammonium oxalate aqueous solution to obtain Residue II, extracting Residue II with 5% NaOH aqueous solution containing 0.05% NaBH$_4$ and filtering to obtain Filtrate I,
neutralizing Filtrate I with AcOH to pH of 5 to 6 to obtain Supernatant I,
adding ethanol to Supernatant I to obtain Precipitate I,
discarding compounds having molecular weight lower than 10,000 from Precipitate I and drying to obtain Fraction I,
extracting Fraction I with 80% formic acid aqueous solution and filtering to obtain Filtrate II,
fractionating Filtrate II by CHCl$_3$-n-BuOH (5:1, v/v) to CHCl$_3$-n-BuOH layer and Aqueous layer I,
extracting Aqueous layer I with 5% lithium chloride-dimethylacetamide aqueous solution to obtain Precipitate II, and further fractionating Precipitate II by ethanol precipitation.

Angiogenesis can be effectively inhibited by applying the method of inhibiting angiogenesis of the present invention.

[2] The above-described a lower aliphatic alcohol or a lower aliphatic alcohol containing not more than 20% of water can be a 80% ethanol aqueous solution.

[3] The above-described 1% ammonium oxalate aqueous solution, 5% NaOH aqueous solution containing 0.05% NaBH$_4$, 80% formic acid aqueous solution and 5% lithium chloride-dimethylacetamide aqueous solution can be 1% ammonium oxalate aqueous solution at 100 degrees C., 5% NaOH aqueous solution containing 0.05% NaBH$_4$ at 30 degrees C., 80% formic acid aqueous solution at 85 degree C. and 5% lithium chloride-dimethylacetamide aqueous solution at 30 degrees C., respectively.

[4] The above-described ethanol added to Supernatant I can be a five times volume of ethanol.

[5] The above-described discarding compounds having molecular weight lower than 10,000 from Precipitate I can be performed by dialyzing.

[6] The above-described drying after dialyzing Precipitate I can be lyophilizing.

[7] In the method of inhibiting angiogenesis of the present invention, the above substance applied can be orally administered.

[8] The method of inhibiting angiogenesis of the present invention are preferably those that inhibit angiogenesis induced by vascular endothelial growth factor (VEGF).

[9] The method of inhibiting angiogenesis of the present invention are preferably those that inhibit angiogenesis by reducing the secretion of vascular endothelial growth factor (VEGF).

The method of inhibiting angiogenesis of the present invention can be used safely and conveniently for a long period, and is capable of effectively inhibiting angiogenesis.

DETAILED DESCRIPTION OF THE INVENTION

Figure 1:
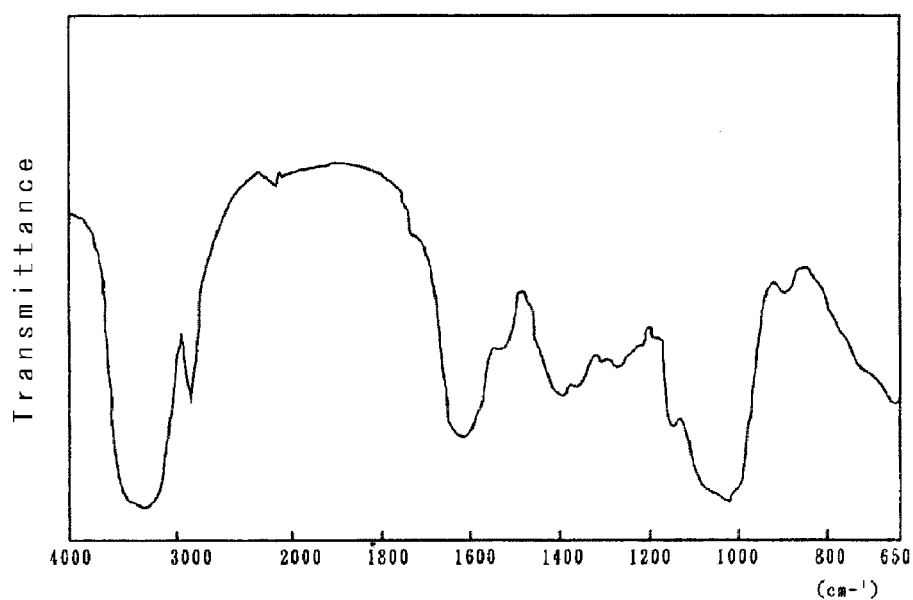
FIG. 1 is an infrared absorption spectrum.

[1] A kind of (1→6)-β-D-glucan protein polysaccharide which is applied for inhibiting angiogenesis in the method of inhibiting angiogenesis of the present invention can, for example, be obtained by the steps of: extracting a fruiting body of *Agaricus blazei* Murill (himematsutake), e.g. a crushed dried fruiting body, with a lower aliphatic alcohol or a lower aliphatic alcohol containing not more than 20% of water, e.g. 80% ethanol aqueous solution, and filtering if necessary, to obtain Residue S,
extracting Residue S with hot water, e.g. hot water at 100 degrees C., and filtering if necessary, to obtain Residue I,
extracting Residue I with 1% ammonium oxalate aqueous solution, e.g. 1% ammonium oxalate aqueous solution at 100 degrees C., and filtering if necessary, to obtain Residue II,
extracting Residue II with 5% NaOH aqueous solution containing 0.05% NaBH$_4$, e.g. 5% NaOH aqueous solution containing 0.05% NaBH$_4$ at 30 degrees C., and filtering to obtain Filtrate I (liquid),
neutralizing Filtrate I with AcOH to pH of 5 to 6 to obtain Supernatant I,
adding ethanol, e.g. a five times volume of ethanol, to Supernatant I to obtain Precipitate I,
discarding compounds having molecular weight lower than 10,000 from Precipitate I, e.g. dialyzing Precipitate I to discard compounds having molecular weight lower than 10,000, and drying, e.g. lyophilizing, to obtain Fraction I,
extracting Fraction I with 80% formic acid aqueous solution, e.g. 5% lithium chloride-dimethylacetamide aqueous solution at 30 degrees C., and filtering to obtain Filtrate II (liquid),
fractionating Filtrate II by CHCl$_3$-n-BuOH (5:1, v/v) to CHCl$_3$-n-BuOH layer and Aqueous layer I,
extracting Aqueous layer I with 5% lithium chloride-dimethylacetamide aqueous solution and filtering if necessary, to obtain Precipitate II, and further fractionating Precipitate II by ethanol precipitation and drying, e.g. freeze drying.

[2] In the method of inhibiting angiogenesis of the present invention, a (1→6)-β-D-glucan-containing product such as a (1→6)-β-D-glucan protein polysaccharide, e.g. a (1→6)-β-D-glucan-containing product derived from the *Agaricus blazei* Murill fruiting body, is applied. The active ingredient of the anti-angiogenic agent in the present invention is a (1→6)-β-D-glucan-containing product such as a (1→6)-β-D-glucan protein polysaccharide.

(1) A (1→6)-β-D-glucan-containing product can, for example, be obtained as described below.

The fresh fruiting body or dried fruiting body of *Agaricus blazei* Murill (himematsutake) is used as shredded for the fresh fruiting body, or as milled for the dry product. The shredded or milled fruiting body is subjected to a pre-extraction treatment with a lower aliphatic alcohol or a lower aliphatic alcohol containing not more than 20% of water to remove low-molecular components.

Next, the residue after extraction is subjected to hot water extraction, and the water-soluble components are removed. This extraction residue is air-dried and subjected to extraction with an aqueous solution of ammonium oxalate. Furthermore, the extraction residue is subjected to extraction at 30 degrees Celsius with the addition of a 5% aqueous solution of sodium hydroxide.

This extract is neutralized with acetic acid and adjusted to a pH of 5 to 6, and the resulting precipitate is removed. Next, the protein polysaccharide component is separated by gel filtration. Furthermore, this was dialyzed and purified by desalinization by another publicly known means of purification; after the purified liquid is concentrated, the concentrate is lyophilized by a conventional method to yield a greyish white powder.

(2) Physicochemical Properties

The physicochemical properties of the above mentioned (1→6)-β-D-glucan-containing product such as a (1→6)-β-D-glucan protein polysaccharide as an active ingredient of the anti-angiogenic agent are described below.

(a) Elemental analysis results

C 41.8%, H 7.15%, N 6.88%; a protein polysaccharide having a sugar content (based on glucose) of 50.2% as determined by the phenol sulfuric acid method and a protein content (based on bovine albumin) of 43.3% as determined by the Lowry method.

The sugar composition mostly comprises glucose as determined by alditol acetate gas chromatography, and contains trace amounts of xylose, galactose, and maltose. Methylation analysis by the Hakomori method and 1H- and 13C-NMR analysis reveal β1-6 bonds of glucose.

(b) The molecular weight as determined by gel filtration is about 10,000 to 50,000.

(c) Optical rotation:
Levorotary under the conditions:

$[\alpha]_D^{25} = -23.0°$ (c=1.0, 5% NaOH)

(d) Results of a determination of the infrared absorption spectrum by the KBr disc method are shown in FIG. 1.

Figure 2:
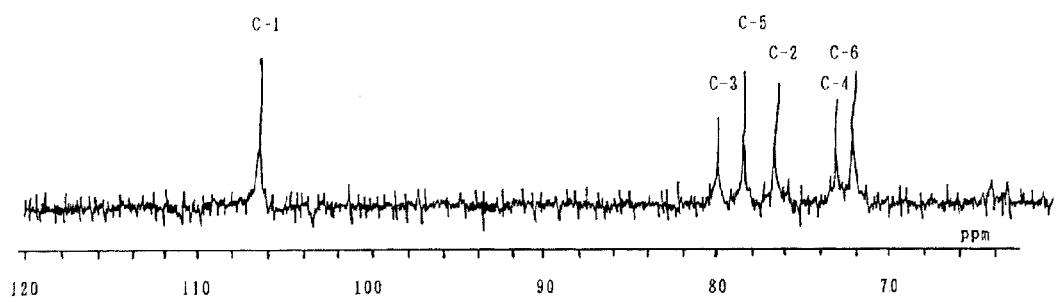
FIG. 2 is a nuclear magnetic resonance spectrum.

(e) Results of a determination of the nuclear magnetic resonance spectrum (13C-NMR) in solution in 0.3M NaOD are shown in FIG. 2.

(f) Soluble in alkalis such as 1 to 10% sodium hydroxide, slightly soluble in water, acids, and DMSO (dimethylsulfoxide), and insoluble in organic solvents, for example, ethanol, acetone, ether, and chloroform.

(g) Positive for the anthrone sulfuric acid reagent and the ninhydrin reaction reagent.

(h) The powder obtained by lyophilization has a greyish white color.

(i) The amino acid composition (mol %)

The product hydrolyzed with 6M hydrochloric acid at 110 degrees Celsius for 20 hours is determined using the Hitachi 835 model amino acid analyzer; the results are Asp 10.7, Thr 5.2, Ser 5.3, Glu 11.1, Gly 9.3, Ala 11.9, Val 4.9, Met 1.1, Ile 3.3, Leu 10.8, Tyr 2.4, Phe 4.5, Lys 5.3, His 2.1, Arg 5.2, Pro 6.9.

(3) Acute Toxicity

In an acute toxicity study in ICR mice (female, 5 weeks of age) by a single intraperitoneal or oral dose (1-week observation), no remarkable body weight change was observed in the mice receiving 500 mg/kg of the above-described (1→6)-β-D-glucan-containing product in the present invention with a mortality rate of 0/7 for both routes of administration (JP-A-HEI-2-78630).

[3] According to the procedure of Kawagishi et al. [Kawagishi H, Kanao T, et al.: Formolysis of a potent antitumor (1-6)-β-D-glucan-protein complex from *Agaricus blazei* fruiting bodies and antitumor activity of the resulting products. Carbohydr Polym 12: 393-403 1990], after extraction of a hot-water-soluble polysaccharide from the fruiting bodies of *Agaricus blazei* Murill (himematsutake), water-insoluble polysaccharides were obtained by successive extraction with 1% ammonium oxalate aqueous solution, 5% sodium hydroxide aqueous solution, 20% sodium hydroxide aqueous solution, and 5% lithium chloride-dimethylacetamide aqueous solution in that order. These water-insoluble fractions were further fractionated by ethanol precipitation, gel-filtration, and the like to yield the test substance (1→6)-β-D-glucan protein polysaccharide, for example a protein polysaccharide of a (1→6)-β-D-glucan with a glucan:protein ratio of 55:43 [w/w].

[4] The (1→6)-β-D-glucan-containing product such as the above-described (1→6)-β-D-glucan protein polysaccharide applied in the method of inhibiting angiogenesis of the present invention or an active ingredient of the anti-angiogenic agent of the present invention is suitable for oral administration; its adult dose is suitably about 0.1 to 10 g per day. However, this is not to be construed as limiting, because (1→6)-β-D-glucan-containing products such as (1→6)-β-D-glucan protein polysaccharidees are not toxic to the human body.

Said (1→6)-β-D-glucan-containing product is not subject to limitations with respect to the dosage form for oral administration, and can, for example, be formulated in powders, tablets, hard capsules, and soft capsules.

In forming various dosage forms, various excipients, binders, disintegrants, lubricants, coating agents, coloring agents, taste correctives, odor correctives, plasticizers, and the like can be used as appropriate.

Examples of excipients include sugars (lactose, sucrose, glucose, mannitol), starches (potato, wheat, corn), inorganic substances (calcium carbonate, calcium sulfate, sodium hydrogen carbonate, sodium chloride), crystalline cellulose, plant powders (licorice powder, gentian powder), and the like.

Examples of binders include starch paste liquid, gum arabic, gelatin, sodium alginate, methylcellulose (MC), ethylcellulose (EC), polyvinylpyrrolidone (PVP), polyvinyl alcohol (PVA), hydroxypropylcellulose (HPC), carboxymethylcellulose (CMC), and the like.

Examples of disintegrants include starches, agar, gelatin powder, crystalline cellulose, CMC-Na, CMC-Ca, calcium carbonate, sodium hydrogen carbonate, sodium alginate, and the like.

Examples of lubricants include magnesium stearate, talc, hydrogenated vegetable oils, macrogol, silicone oil, and the like.

Examples of coating agents include sugar coatings (sucrose, HPC, shellac), glue coatings (gelatin, glycerine, sorbitol), film coatings [hydroxypropylmethylcellulose (HPMC), EC, HPC, PVP], enteric coatings [hydroxypropylmethylcellulose phthalate (HPMCP), cellulose acetate phthalate (CAP)], and the like.

Examples of coloring agents include water-soluble food dyes, lake pigments, and the like. Examples of taste correctives include lactose, sucrose, glucose, mannitol, and the like. Examples of odor correctives include aromatic essential oils), light screens (titanium oxide) and the like. Examples of plasticizers include phthalic acid esters, vegetable oils, polyethylene glycol, and the like.

The food/beverage composition for angiogenesis inhibition of the present invention can be in, for example, a form containing a (1→6)-β-D-glucan-containing product such as a (1→6)-β-D-glucan protein polysaccharide in a food/beverage composition that constitutes a nutritional food, nutritional supplement, beverage, or the like, and may comprise various components that do not interfere with the effect of the present invention.

Such method of inhibiting angiogenesis of the present invention can be used safely and conveniently for a long period, and is capable of effectively inhibiting angiogenesis. Such anti-angiogenic agents and food/beverage compositions for anti-angiogenic agents can be administered safely and conveniently for a long period, and are capable of effectively inhibiting angiogenesis.

EXAMPLES

A kind of (1→6)-β-D-glucan protein polysaccharide [hereinafter also referred to as "ABP"] was tested for anti-angiogenic effects in oral administration.

(1) Test Substance and Test Animals

The test substance was obtained as below.

Dried fruiting bodies of *Agaricus blazei* Murill (himematsutake) were crushed and extracted with 80% ethanol aqueous solution six times and filtered to obtain Residue S.

Residue S was extracted with hot water at 100 degrees C. for 61.3 hours seven times and filtered to obtain Residue I.

Residue I was extracted with 1% ammonium oxalate aqueous solution at 100 degrees C. for 31.5 hours six times and filtered to obtain Residue II.

Residue II was extracted with 5% NaOH aqueous solution containing 0.05% $NaBH_4$ at 30 degrees C. for 20 hours and filtered to obtain Filtrate I (liquid).

Filtrate I was neutralized with AcOH to pH of 5 to 6 to obtain Supernatant I. A five times volume of ethanol was added to Supernatant I to obtain Precipitate I.

Precipitate I was dialyzed to discard compounds having molecular weight lower than 10,000 and lyophilized to obtain Fraction I.

Fraction I was extracted with 80% formic acid aqueous solution at 85 degree C. for 45 minutes and filtered to obtain Filtrate II (liquid).

Filtrate II was fractionated by $CHCl_3$-n-BuOH (5:1, v/v) to $CHCl_3$-n-BuOH layer and Aqueous layer I.

Aqueous layer I was extracted with 5% lithium chloride-dimethylacetamide aqueous solution at 30 degrees C. thirty times and filtered to obtain Precipitate II.

Precipitate II was further fractionated by ethanol precipitation and freeze dried to yield Fraction II as the test substance.

Fraction II was obtained in high yield, i.e. 11.93 g of Fraction II was obtained relative to 985 g of dried fruiting bodies of *Agaricus blazei* Murill (himematsutake).

Five-week-old female A/J Jms Slc mice weighing 15-20 g (obtained from Japan SLC, Inc.) were used as test animals. These mice maintained on a CE-7 pellet diet (produced by CLEA Japan, Inc.) with free access to water.

(2) Measurement of Tumor-Induced Angiogenesis in the Dorsal Air Sac (DAS) Assay

DAS assay was carried out according to the method described by Yamamoto et al. [Yamamoto K, Kimura T,: Anti-angiogenic and anti-metastatic effects of β-1,3-D-glucan purified from Hanabiratake, *Sparassis crispa*. Biol Pharm Bull 32(2): 259-263 2009] with a slight modification.

Specifically, both sides of a diffusion chamber ring were covered with membrane filters; the resulting chambers were filled with $5 \times 10^5$ cells of P-7423 cells (lung tumor cells 7423) in 150 μL of PBS. Each P-7423 containing chamber was implanted into the DAS of female A/J Jms Slc mice on day 0. The control group was implanted with PBS containing chamber. In all cases, the PBS was an antibacterial/antifungal solution containing 10,000 U/mL penicillin in phosphate-buffered physiological saline (×100) (produced by Wako Pure Chemical Industries).

ABP was orally administered twice a day from day 1 to day 14.

Figure 3:
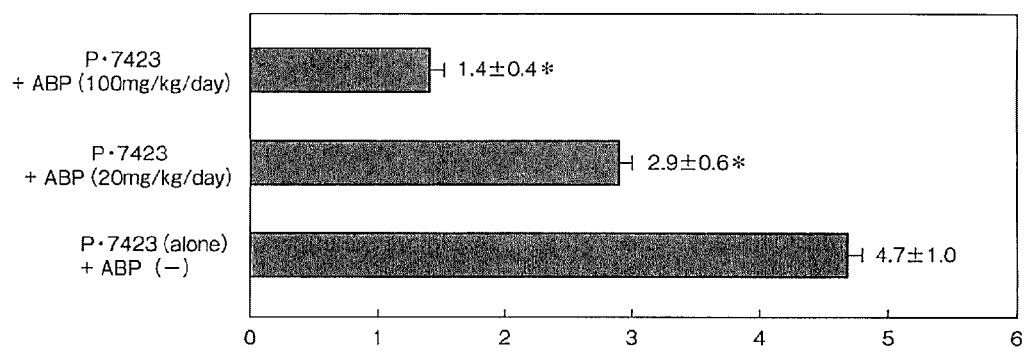
FIG. 3 is a graphic representation showing the influence of (1→6)-β-D-glucan protein polysaccharide on tumor-induced vascularization as determined by the dorsal air sac assay.

On day 15, each mouse was sacrificed and tumor cell-induced angiogenesis at the implanted zone was observed. FIG. 3 shows the number of newly formed blood vessels longer than 3 mm in length with a characteristic zigzag shape of newly formed blood vessels in the chamber implanted zone. In FIG. 3, values are indicated as the mean±standard error (n=7); * indicates a statistically significant difference (p<0.05, versus P-7423-alone control group).

Angiogenesis was strongly induced after implantation of P-7423 cells in the chamber; however, oral administration of ABP significantly inhibited the tumor-induced angiogenesis.

(3) Measurement of VEGF-Induced Angiogenesis in the Matrigel Plug Assay

The Matrigel plug assay was performed according to the method described by Passaniti et al. [Passaniti A, Taylor R M, et al.: A simple, quantitative method for assessing angiogenesis and antiangiogenic agents using reconstituted basement membrane, heparin, and fibroblast growth factor. Lab Invest 67: 519-528 1992].

Specifically, each female A/J Jms Slc mice was subcutaneously injected with 0.5 mL of Matrigel containing 20 ng/mL of VEGF (recombinant mouse VEGF, obtained from Sigma Co., [USA]) and 32 U/mL heparin on day 0. The control group was injected with Matrigel alone.

ABP was orally administered twice a day from day 1 to day 14.

On day 15, each Matrigel was excised and weighed, and then the gel was treated with dispase-II (1.5 mg/mL, produced by Roche Diagnostics Co.), followed by determination of hemoglobin content using the Quantichrom Hemoglobin assay kit (produced by FUNAKOSHI Co., Ltd.). The results are shown in FIG. 4.

Figure 4:
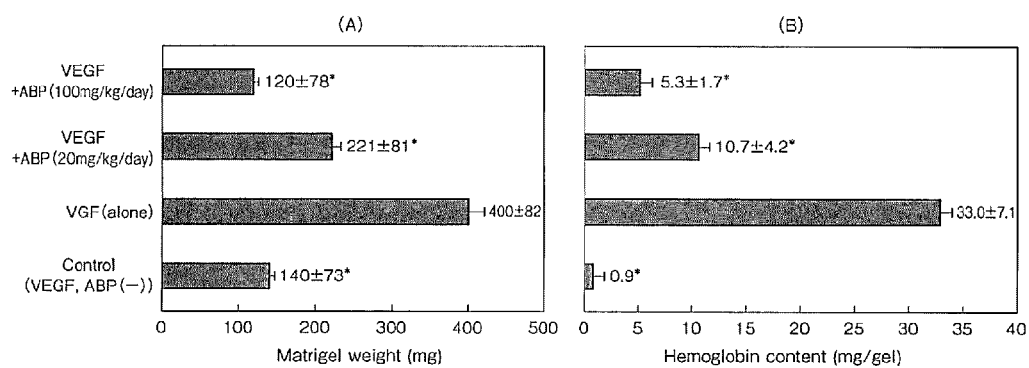
FIG. 4 is a graphic representation showing the influence of (1→6)-β-D-glucan protein polysaccharide on VEGF-induced angiogenesis as determined by Matrigel plug assay.

In FIG. 4, (A) shows Matrigel weight, and (B) shows the hemoglobin content in Matrigel. In FIG. 4, values are indicated as the mean±standard error (n=7); * indicates a statistically significant difference (p<0.05, versus VEGF-alone control group).

Remarkable increase in the Matrigel weight and the hemoglobin content was observed in the group injected with Matrigel containing VEGF compared to the group treated with Matrigel alone. Conversely, such angiogenic responses were significantly suppressed by oral administration of ABP.

(4) VEGF Secretion in P-7423 (Lung Tumor Cells 7423) Cells

P-7423 lung carcinoma cells were grown in 24 well plates in complete medium and incubated at 37 degrees Celsius, 5% gaseous carbon dioxide for 24 hours).

The medium was replaced with RPMI-1640 (a single-cell suspension of $5 \times 10^5$ viable cells of P-7423 line) with FBS (fetal bovine serum, obtained from Gibco BRL Co. [New Zealand]) and the 0, 20, 200 μg/mL ABP, and incubated at 37 degrees Celsius, 95% nitrogen/5% gaseous carbon dioxide for 18 hours in hypoxia, after which conditioned media were analyzed for VEGF protein content by an ELISA kit (produced by Santa Cruz Biotechnology, Inc.).

Table 1 shows the effect of ABP on VEGF expression in culture supernatants of P-7423 cell in hypoxia as VEGF (pg/mL) of P-7423 cells at each ABP concentration. In Table 1, each value is shown as the mean±standard error (n=4); * indicates a statistically significant difference (p<0.01, versus control group).

TABLE 1

| ABP dose (μg/ml) | VEGF (pg/ml) of P · 7423 in hypoxia |
|---|---|
| 0 | 262.5 ± 22.4 |
| 20 | 259.7 ± 30.1 |
| 200 | 228.0 ± 20.5* |

As shown in Table 1, 200 μg/mL ABP decreased the secreted VEGF content significantly.

(5) HUVEC Proliferation Assays

Angiogenesis depends on several aspects such that the endothelial cells must proliferate to provide the necessary number of cells for the growing vessels, and the cells need to be capable of migration, etc. Due to the key role vascular endothelial cell plays in angiogenesis, the effect of ABP on HUVEC was explored.

HUVEC (human umbilical venous endothelial cells, obtained from Kurabo Industries Co.) were suspended in a DMEM (Dulbecco's modified Eagle medium, obtained from Nissui Pharmaceutical Co.,) with 2% (v/v) FBS (fetal bovine serum, obtained from Gibco BRL Co. [New Zealand]) (40,000 cells/mL), plated onto gelatinized 96-well culture plates (0.1 mL/well), and incubated (37 degrees Celsius, 5% gaseous carbon dioxide for 24 hours).

The medium were replaced with 0.1 mL of the DMEM with 5% (v/v) FBS, and incubated for 24, 48, and 72 hours, or with the addition of 2, 20, 200 µg/mL ABP (for 48 hours, 37 degrees Celsius, 5% gaseous carbon dioxide). Cell proliferation was determined using MTT assay (Carmichael J, DeGraff W G, et al.: Evaluation of a tetrazolium-based semi-automated colorimetric assay. Assessment of chemosensitivity testing. Cancer Res 47: 936-942 1987). The results are shown in FIG. 5.

Figure 5:
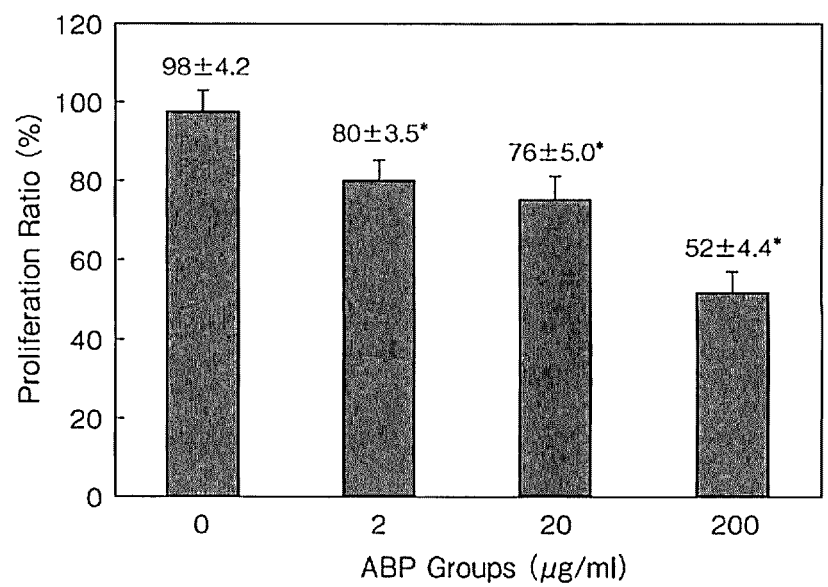
FIG. 5 is a graphic representation showing the human umbilical venous endothelial cell proliferation inhibitory effect of (1→6)-β-D-glucan protein polysaccharide.

In FIG. 5, the proliferation ratio (%) indicates the cell proliferation rate in different dose ABP medium compared with DMEM when cell numbers are considered as 100%. In FIG. 5, each value is shown as the mean±standard error (n=6); * indicates a statistically significant difference ($p<0.05$, versus DMEM-treated control group).

ABP at 2, 20, 200 µg/mL inhibited the proliferation of HUVEC in a dose-dependent fashion.

Specifically, ABP was shown to directly inhibit HUVEC cell proliferation in vitro. However the mechanism of ABP inhibitory effect on HUVEC is unclear, which could be the cytotoxicity effect.

It has already been found that tumor-induced neovascularization is inhibited by ergosterol isolated from *Agaricus blazei*. Fungal protein-bound polysaccharide (Krestin) derived from *C. vesicolor* was also reported to act as an anti-angiogenic agent.

However, Krestin is mainly constituted of β-1,4-bond glucan main chain having β-1,3 and β-1,6 bond side chain binding to a protein moiety.

Therefore, it is considered that ABP having (1→6)-β-D-glucan is a novel anti-angiogenic agent being particularly effective in oral administration.

What is claimed is:

1. A method of inhibiting angiogenesis by applying a substance obtained by the steps of:
    extracting a fruiting body of *Agaricus blazei* Murill (himematsutake) with a lower aliphatic alcohol or a lower aliphatic alcohol containing not more than 20% of water to obtain Residue S,
    extracting Residue S with hot water to obtain Residue I,
    extracting Residue I with 1% ammonium oxalate aqueous solution to obtain Residue II,
    extracting Residue II with 5% NaOH aqueous solution containing 0.05% $NaBH_4$ and filtering to obtain Filtrate I,
    neutralizing Filtrate I with acetic acid to pH of 5 to 6 to obtain Supernatant I,
    adding ethanol to Supernatant I to obtain Precipitate I,
    discarding compounds having molecular weight lower than 10,000 from Precipitate I and drying to obtain Fraction I,
    extracting Fraction I with 80% formic acid aqueous solution and filtering to obtain Filtrate II,
    fractionating Filtrate II by $CHCl_3$-n-butanol (5:1, v/v) to $CHCl_3$-n-butanol layer and Aqueous layer I,
    extracting Aqueous layer I with 5% lithium chloride-dimethylacetamide aqueous solution to obtain Precipitate II, and
    further fractionating Precipitate II by ethanol precipitation.

2. The method according to claim 1 wherein a lower aliphatic alcohol or a lower aliphatic alcohol containing not more than 20% of water is 80% ethanol aqueous solution.

3. The method according to claim 1 wherein 1% ammonium oxalate aqueous solution, 5% NaOH aqueous solution containing 0.05% $NaBH_4$, 80% formic acid aqueous solution and 5% lithium chloride-dimethylacetamide aqueous solution are 1% ammonium oxalate aqueous solution at 100 degrees C., 5% NaOH aqueous solution containing 0.05% $NaBH_4$ at 30 degrees C., 80% formic acid aqueous solution at 85 degree C. and 5% lithium chloride-dimethylacetamide aqueous solution at 30 degrees C., respectively.

4. The method according to claim 1 wherein the ethanol added to Supernatant I is a five times volume of ethanol.

5. The method according to claim 1 wherein discarding compounds having molecular weight lower than 10,000 from Precipitate I is performed by dialyzing.

6. The method according to claim 5 wherein drying after dialyzing Precipitate I is lyophilizing.

7. The method according to claim 1 wherein the above substance applied is a preparation for oral administration.

8. A method of inhibiting angiogenesis by applying a substance obtained by the steps of:
    extracting a crushed dried fruiting body of *Agaricus blazei* Murill (himematsutake) with 80% ethanol aqueous solution to obtain Residue S,
    extracting Residue S with hot water at 100 degrees C. to obtain Residue I,
    extracting Residue I with 1% ammonium oxalate aqueous solution at 100 degrees C. to obtain Residue II,
    extracting Residue II with 5% NaOH aqueous solution containing 0.05% $NaBH_4$ at 30 degrees C. and filtering to obtain Filtrate I,
    neutralizing Filtrate I with acetic acid to pH of 5 to 6 to obtain Supernatant I,
    adding a five times volume of ethanol to Supernatant I to obtain Precipitate I,
    dialyzing Precipitate I to discard compounds having molecular weight lower than 10,000 and lyophilizing to obtain Fraction I,
    extracting Fraction I with 80% formic acid aqueous solution at 85 degree C. and filtering to obtain Filtrate II,
    fractionating Filtrate II by $CHCl_3$-n-butanol (5:1, v/v) to $CHCl_3$-n-butanol layer and Aqueous layer I,
    extracting Aqueous layer I with 5% lithium chloride-dimethylacetamide aqueous solution at 30 degrees C. to obtain Precipitate II, and
    further fractionating Precipitate II by ethanol precipitation.

* * * * *